United States Patent [19]

van der Stoel et al.

[11] Patent Number: 4,473,699

[45] Date of Patent: Sep. 25, 1984

[54] PROCESS FOR THE PREPARATION OF INDOLE AND SKATOLE

[75] Inventors: Roland E. van der Stoel, Buchten; Petrus H. J. Janssen, Geleen; Cornelis G. M. van de Moesdijk, Elsloo, all of Netherlands

[73] Assignee: Stamicarbon B.V., Geleen, Netherlands

[21] Appl. No.: 377,139

[22] Filed: May 11, 1982

[30] Foreign Application Priority Data

May 15, 1981 [NL] Netherlands ......................... 8102390

[51] Int. Cl.$^3$ .......................................... C07D 209/08
[52] U.S. Cl. ..................................................... 548/508
[58] Field of Search ........................ 548/508; 546/181

[56] References Cited

U.S. PATENT DOCUMENTS 3,007,931 11/1961 Simpson et al. .................... 546/181
3,950,438 4/1976 Schaafsma et al. .

FOREIGN PATENT DOCUMENTS 684736 4/1964 Canada ................................ 548/508

5062061 10/1978 Japan ................................... 548/508

OTHER PUBLICATIONS

Journal of Organic Chemistry 28, 3442, (1963).
Preparation of Catalysts II, pp. 265–274, van den Berg et al.
Fenaroli's Handbook of Flavor Ingredients, vol. II, Second Ed., CRD Press, (1975).
Journal of Organic Chemistry 27 3882–3885, 1962.
Chemische Berichte 95, pp. 307–318, 1962.

Primary Examiner—Richard Raymond
Assistant Examiner—D. B. Springer
Attorney, Agent, or Firm—Cushman, Darby & Cushman

[57] ABSTRACT

Indole, and/or methyl-substituted indoles are described as prepared from the corresponding 2-(cyanomethyl)-cyclohexanone starting material through a catalytic reaction in the presence of hydrogen, using a metal, or metal compound, of Group VIII or Group Ib of the Periodic Table. The reaction is carried out at an elevated temperature at high conversion to yield the corresponding indole and (in some cases) tetra- or hexahydroindoles.

5 Claims, No Drawings

PROCESS FOR THE PREPARATION OF INDOLE AND SKATOLE

The invention relates to a process for the preparation of indole, including indoles which may be substituted with a methyl group at one or more of the C atoms in the positions 3, 4, 5, 6 and 7. The product may also include the corresponding hydrogenated product, for instance, tetrahydroindole.

Indole, and its methyl-substituted derivatives are utilized, for instance, in the fragrances industry, and are generally commercially recovered from coal tar. However, as a result of the very low concentration in coal tar of the compounds concerned (approximately 0.2% by weight) this recovery is very expensive. Up to now, a suitable method for the commercial synthetic preparation of indole and the said methyl-substituted indole compounds has not been known. The present invention now provides such a method.

According to this invention, the process for the preparation of indole, which may be substituted, with a methyl group at one or more of the C atoms in the positions 3, 4, 5, 6 and 7, possibly mixed with the corresponding hydrogenated product, is characterized in that 2-(cyanomethyl)-cyclohexanone, in which an H atom of one or more of the $CH_2$ groups may have been replaced by a methyl group, is contacted in the gas phase and in the presence of hydrogen, with a dehydrogenation-catalyst containing a metal from the Group VIII or Group Ib of the Periodic Table of elements (Lange's Handbook of Chemistry, 11th Edition), or a compound of such a metal, to form a reaction mixture containing indole or the corresponding substituted indole and possibly, the corresponding hydrogenated product.

It is already known to cyclize 2-(cyanomethyl)-cyclohexanone (2-oxocyclohexaneacetonitrile) (Journal of Organic Chemistry 27 3882–3885, 1962). However, the process involves a cyclization in the liquid phase with the very costly $LiAlH_4$ reagent, and in which no indole, but only hexahydroindole, is formed, the yield being 25%. Also known (Chemische Berichte 95, pp. 307–318, 1962) is the hydrogenation of cyclohexanone-(2)-1-cyanacetic ester, in which also only the hydrogenated product is obtained.

By preference, the present catalyst is a metal or a compound of a metal, e.g. an oxide, from the group consisting of platinum, palladium and rhodium. The other metals of said Group VIII or Group Ib may also be employed.

These catalysts can be employed on a supporting material such as activated carbon, graphite, silicon oxide, zinc oxide, aluminum oxide, magnesium oxide and mixtures of these materials. As such, a supporting material aluminum oxide is particularly suitable. A promoter can also be added to the catalyst. As such, by preference an alkali metal or alkali metal compound e.g. an oxide is employed. The amount of supporting material can vary, for instance in such a way that the quantity of catalyst amounts to 0.01–10% by weight (calculated as metal and based on the total amount of catalyst material including the support). The amount of promoter, if employed, can also vary e.g. between 0.01 and 2% by weight (calculated as metal and based on the total amount of catalyst material including the support).

The dehydrogenation-catalysts which are used in the process according to the invention are already known in themselves and can be prepared for instance by treating the support with a salt of the concerning metal followed by calcination and reduction in the manner described on page 265 of Preparation of Catalyts II by G. H. van den Berg and H. Th. Rynten (Elsevier Amsterdam 1979), the disclosure of which is incorporated herein by reference.

The process according to this invention can be carried out at various temperatures, for instance, at a temperature of 175° to 350° C. Advantageously, a temperature of between 200° and 310° C. is applied.

Procedurally, the process according to this invention can be carried out by techiques already known in themselves for conducting catalytic gas-phase reactions; for instance, by leading the gaseous starting material, optionally diluted with an inert gas such as nitrogen, together with hydrogen over the catalyst in the form of a fixed bed, using a space velocity of between, for instance, 0.03 and 3 g starting material per ml catalyst (compacted volume) per hour, advantageously from 0.5 to 2 g per mole per hour.

The amount of hydrogen used can vary from 1 to 50 moles of hydrogen per mole of starting material. Use of more than 50 moles hydrogen per mole starting material is also possible, but this does not result in any advantage.

The starting compound itself can be obtained by reaction of cyclohexanone, or the related methyl substituted cyclohexanone, with chloroacetonitrile or 2-chloropropionitrile in the manner described in the above-cited publication in the Journal of Organic Chemistry, the disclosure of which is incorporated herein by reference.

By cooling the gaseous reaction mixture obtained from the process according to this invention, a separation can be achieved into a condensate and a hydrogen-containing gas which can be recycled. The condensate obtained can, for instance, then be separated by fractional distillation, and the unreacted starting material can be recycled, if desired.

In the following non-limiting Examples, the invention will be further elucidated.

EXAMPLE I

Through a vertical tubular reactor (17 mm diameter, 400 mm length) in which there is a catalyst zone of 10 ml (compacted volume), a gaseous mixture of 2-oxocyclohexaneacetonitrile and hydrogen (30 moles hydrogen per mole of the oxonitrile) is passed from top to bottom, over a period of 4 hours.

The catalyst zone is bounded at the bottom by a zone of 5 ml and at the top by a zone of 100 ml inert ceramic material. As catalyst palladium and sodium on γ-aluminumoxide (0.5 wt. % Pd and 0.4 wt. % Na). Per ml catalyst (compacted volume) 0.15 g of 2-oxocylohexaneacetonitrile is fed through per hour.

The temperature of the catalyst and the inert material is kept at 300° C. by means of a heating jacket around the reactor. After 3 hours, the composition of the reaction mixture obtained is determined by passing the mixture for 1 hour through a small vessel which has been cooled to 0° C. and by analyzing the condensed product thus-obtained by gas-chromatograph.

From this analysis and the weight of the amount of 2-oxocyclohexaneacetonitrile which has been passed through in the period of 1 hour, the conversion of the oxonitrile and the yields of indole, tetrahydroindole and hexahydroindole can be readily determined.

Conversion is understood to mean the amount of oxonitrile which has been converted (amount of oxonitrile passed through minus amount of oxonitrile in the condensed product) expressed as a percentage of the amount of oxonitrile passed through. The yield of indole, tetrahydroindole and hexahydroindole, respectively, is understood to mean the amount of indole, tetrahydroindole and hexahydroindole, respectively, in the condensed product, expressed as a percentage of the amount of idole, tetrahydroindole and hexahydroindole, respectively, which can theoretically be formed from the converted amount of oxonitrile.

In this Example, the conversion of the oxonitrile amounts to 75% and the indole yield is 27%.

EXAMPLE II

In the manner described in Example 1, a mixture of 2-oxocyclohexaneacetonitrile and hydrogen is passed over a catalyst composed of platinum and γ-aluminumoxide (0.5 wt. % platinum). The oxonitrile conversion is 69%, and the yields are indole 11%, tetrahydroindole 12% and hexahydroindole 1%.

EXAMPLE III

In the manner described in Example I, but differing in that the temperature of the catalyst and the inert material is kept at 240° C., a mixture of 2-oxocyclohexaneacetonitrile and hydrogen is passed over a catalyst composed of platinum on γ-aluminumoxide (0.5 wt. % Pt). The oxonitrile conversion is 100%, and the yields are indole 18%, tetrahydroindole 19% and hexahydroindole 1%.

EXAMPLE IV

In the manner described in Example III, a mixture of 2-oxocyclohexaneacetonitrile and hydrogen is passed over a catalyst composed of rhodium on γ-aluminumoxide (0.5 wt. % Rh). The conversion of the oxonitrile is 99%, and the yields are indole 9%, tetrahydroindole 26% and hexahydroindole 5%.

EXAMPLE V

In the manner described in Example IV, for 7 hours a mixture of 2-oxocyclohexaneacetonitrile and hydrogen is passed over a catalyst composed of palladium and sodium on γ-aluminumoxide (0.5 wt. % Pd and 0.4 wt. % Na). After 6 hours, the composition of the reaction mixture obtained is determined in the way described in Example I. The conversion of the oxonitrile is 93%, the indole yield is 55%, the tetrahydroindole yield is 12% and the hexahydroindole yield is 3%.

EXAMPLE VI

Example V is repeated using 2-(2-oxoxyclohexane)-propionitrile as starting compound. The conversion of the oxonitrile is 85%. The 3-methylindole (skatole) yield is 45%, the 3-methyltetrahydroindole yield is 10% and the 3-methylhexahydroindole yield is 2%.

EXAMPLE VII

Example V is repeated with (4-methyl-2-oxocyclohexane)acetonitrile as starting compound. The oxonitrile conversion is 90%, the 6-methylindole yield is 50%, the 6-methyltetrahydroindole yield is 9% and the 6-methylhexahydroindole yield is 1%.

In the above Examples, the rate of introduction of the starting material per milliliter of compacted catalyst is generally as shown in Example I, for the foregoing Examples, such rate may be varied as indicating hereinabove, while still producing high conversions of the oxonitrile with good yields of the indole and/or hydroindoles.

What is claimed is:

1. A process for the preparation of indole, and/or skatole from the corresponding 2-(cyanomethyl)cyclohexanone starting material, wherein said starting material in the gas phase and in the presence of hydrogen, is passed through a bed of a solid dehydrogenation-catalyst at a temperature from 175° C. to 350° C. to form a reaction mixture, said catalyst consisting essentially of a metal or a compound of a metal selected from the group consisting of platinum, palladium and rhodium, said reaction mixture consisting essentially of said indole or said skatole.

2. Process according to claim 1, wherein said catalyst further consists essentially of an alkali metal or alkali metal compound as a promoter.

3. Process according to claim 1 or 2, wherein the catalyst metal is distributed on aluminumoxide as supporting material.

4. Process according to claim 1 or 2, wherein 1–50 moles hydrogen is employed per mole of starting material.

5. Process according to claim 1 or 2, wherein said starting material is passed through said bed at a rate of 0.03 to 2 g of material per ml (compacted volume) of said solid catalyst per hour.

* * * * *